Figure 4:
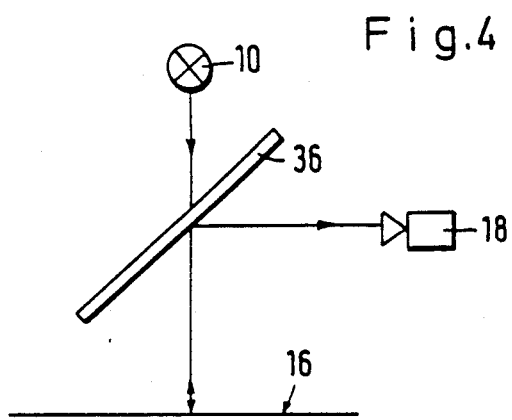

United States Patent [19]

Hatji

[11] Patent Number: 4,891,530
[45] Date of Patent: Jan. 2, 1990

[54] TESTING OR INSPECTING APPARATUS AND METHOD FOR DETECTING DIFFERENTLY SHAPED SURFACES OF OBJECTS

[75] Inventor: Günter H. Hatji, Hamburg, Fed. Rep. of Germany

[73] Assignee: Helmut K. Pinsch GmbH & Co., Hamburg, Fed. Rep. of Germany

[21] Appl. No.: 17,353

[22] Filed: Feb. 24, 1987

Related U.S. Application Data

[63] Continuation of Ser. No. 223,690, Jul. 22, 1988, Pat. No. 4,827,142, which is a continuation-in-part of Ser. No. 846,591, Mar. 31, 1986, abandoned.

[51] Int. Cl.$^4$ ............................................. G01N 21/88
[52] U.S. Cl. ..................................... 250/572; 356/431
[58] Field of Search ............... 250/560, 561, 562, 563, 250/571, 572; 356/383, 430, 431; 364/475, 507

[56] References Cited

U.S. PATENT DOCUMENTS

| | | | |
|---|---|---|---|
| 3,920,970 | 11/1975 | Slaker | 250/563 |
| 3,958,127 | 5/1976 | Faulhaber et al. | 250/563 |
| 4,403,294 | 9/1983 | Hamada et al. | 250/562 |

Primary Examiner—David C. Nelms
Assistant Examiner—William L. Oen
Attorney, Agent, or Firm—Stanger, Michaelson, Reynolds, Spivak & Tobia

[57] ABSTRACT

In a testing or inspecting apparatus for the detection of objects, which have differently formed surfaces and are moved relative to the testing apparatus, the object (12) to be tested is illuminated in a plane at right angles to the main movement direction (arrow 14) with substantially an identical intensity over a narrow zone extending over the width of the object. A detection device detecting the reflected brightness and/or color values of the object, responding to changes to the detected values in the illuminated plane, supplies an information signal, which is interpreted by a computer (FIG. 1).

17 Claims, 2 Drawing Sheets

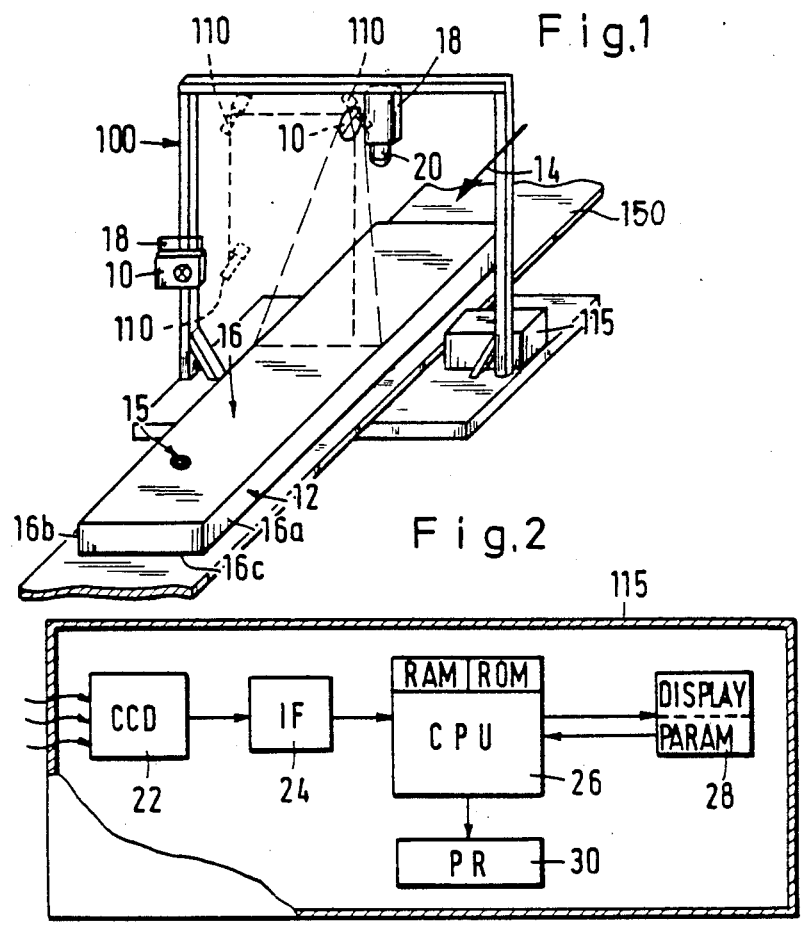
Fig.1
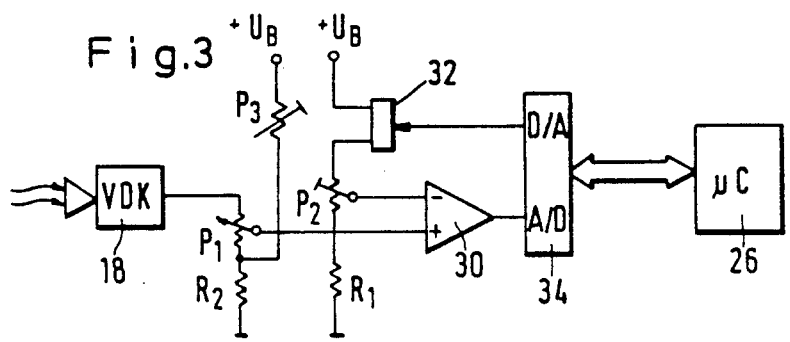
Fig.2
Fig.3

TESTING OR INSPECTING APPARATUS AND METHOD FOR DETECTING DIFFERENTLY SHAPED SURFACES OF OBJECTS

This is a continuation-in-part of prior copending application Ser. No. 846,591, filed Mar. 31, 1986, and now abandoned in favor of Ser. No. 223,690, filed July 22, 1988, now U.S. Pat. No. 4,827,142.

The invention relates to a testing or inspecting apparatus and to a method for detecting differently shaped surfaces of objects, such as ceramic products, glass articles, wood, plastics, objects packed in see-through foil, etc.

Among testing apparatuses, for example those for timber, particularly sawn timber are known. In such known sawn timber testing apparatuses, on one side a mechanical momentum is applied to the sawn timber board to be tested. By means of several sensors located at predetermined distances along the board, the amplitude response of the resulting impact wave is measured. The data supplied by the sensors are fed into a process computer, which determines the modulus of elasticity between the sensors from the measured transit times. Conclusions can be drawn regarding the existence of a timber defect in the board from deviations from the standard values.

However, this method can only be used in the case of boards having the same length. If for the next load production is to be changed to different lengths, a relatively complicated adaptation is in each case necessary.

In addition, this known method does not make it possible to reliably detect all timber defects which occur in the same way, including colour defects, which cannot be detected. Another disadvantage is that the sensors must be applied again to each board to be measured. Continuous operation is impossible.

It is also known to detect and store in linewise manner an image by means of an optical detection system based on the commercial television camera. The stored image data are then fed to a computer, which subjects them to an iconic and/or symbol-oriented processing.

It is a disadvantage of such a method that for high resolution a correspondingly high storage capacity is required. This disadvantage is particularly serious, if different types of images or pictures have to be stored, because then a separate memory zone must be reserved for each image.

The problem of the present invention is to provide a testing apparatus and a method for detecting differently shaped surfaces of objects, which make it possible to speedily and reliably detect special features of the objects to be detected, without complicated precautions being necessary in connection with storage.

According to the invention this problem is solved by a testing apparatus for detecting differently shaped surfaces of objects according to the type described hereinbefore, which is inventively constructed in such a way that the object to be tested can be moved relative to the testing apparatus in a main movement direction, that the object can be illuminated in a plane at right angles to the main movement direction with substantially the same intensity and that an optical detection device is provided in said plane, which detects in line form the reflected brightness and/or colour values of the object, responding to brightness and/or colour changes in the illuminated plane of the object detected by the detection device and during the relative movement of the object and optical detection device supplies an information signal.

The problem is also solved by a detection method, according to which the objects are moved continuously in a main movement direction relative to an optical detection device by absolute movement of the optical detection device or objects, a narrow region extending over the width of the object in a plane extending at right angles to the main movement direction is illuminated and the optical detection device operates in the plane at right angles to the movement direction of the object and responding to brightness and/or colour changes to the object during the relative movement of object and optical detection device supplies an information signal.

It is particularly advantageous that continuous operation of the testing apparatus and consequently on-line use is made possible by real time detection. For example, when using sawn timber as the object to be tested, it is possible to rapidly and reliably detect timber defects which occur, such as e.g. branch knots, red rot and the like. It is also possible to determine the fault or defect points in piece and position-related manner, so that suitable sections with a given and desired fault-free length can be determined, so that sawn timber of a lower quality category can be used for higher quality purposes.

The optical detection device is connected to a computer. The latter has a store, in which the information signals which occur are stored.

Due to the fact that an optical method is used, it is initially possible to achieve the advantage that colour defects can also be recorded. Thus, it is possible, in response to brightness or colour differences or to a combination of brightness and colour differences, to supply an information signal, which can indicate the position of the particular feature. The latter is e.g. constituted by a defect in a piece of sawn timber, a crack in a flagstone or glazed tile, a colour defect therein, a discolouration of an article packed in see-through foil, etc. As no sensors have to be applied to each object, continuous operation is possible. For example, the testing apparatus can be fixed and the objects moved by the testing apparatus, so that e.g. timber can be tested at a speed of 3 m/s.

A particular advantage is that despite continuous operation, the apparatus makes it possible to detect defects in piece-related manner. Thus, with respect to each stored object, particularly each piece of timber, it is possible to store the fault-free length, i.e. the length between any faults, in addition to the absolute length. If sawn timber of a particular fault-free length is required, then it is possible to rapidly determine the most suitable piece of sawn timber for this purpose. The same also applies with regards to the testing of wood veneers.

Thus, it is possible to use for a higher quality purpose sawn timber from a lower quality class according to DIN 68256.

According to the invention, there is no need for the hitherto necessary visual check of the objects to be tested, e.g. the wood, which is very tiring for the eyes of the tester.

Advantageous further developments can be gathered from the subclaims.

The information signal supply can be interpreted through linking the optical detection device and the computer. The latter is chosen in such a way that it has an adequate speed to be able to process the incoming information signals in real time. However, appropriately, but not necessarily, the information signals which occur are sequentially stored in a memory.

The invention also relates to a construction in which the computer has a time or length measuring device, which measures the time or length from the detection of the leading edge of an object, viewed in the main movement direction, until the information signal occurs, the time or length measuring device being connected to the memory.

According to another development of the invention, a matching circuit (interface) is provided, which makes it possible to adjust an identification threshold for the information signal. In addition, the matching circuit can have in particular electronic control elements for matching the optical detection device or the light source to different brightnesses of the surface of the tested objects or the light source utilizing the maximum dynamics of the optical detection device.

The optical detection device also appropriately has a filter for increasing the sensitivity for particular features of the objects to be tested and which are to be determined.

The optical detection device with the light source is positioned on a support frame, which e.g. surrounds the objects to be detected in annular manner, whereby optical detection devices with light sources can be provided, as a function of the detection surface, at the top and/or bottom and/or on the sides of the support frame. It is also possible to use only a single light source, so that the support frame in this embodiment then carries a corresponding number of reflecting mirrors arranged in such a way that only specific surfaces of the object to be detected or all the surfaces thereof are illuminated. This also applies to the optical detection device directed by means of reflecting mirrors on to the surface or surfaces to be detected, so that apart from a number of optical detection devices corresponding to the number of surfaces to be detected, it is also possible to use only a single optical detection device. The different light intensities of the illuminated surfaces can then be used as a distinguishing feature to establish which of the surfaces is being detected at the instant of detection, so as to obtain the necessary information signal. It is also possible to successively determine the different surfaces of the object in a given time frame or slot pattern and to store the values obtained.

It is particularly advantageous for the scanning to take place in lines. The line extends at right angles to the main movement direction of the object. If a defect is detected within a line, this leads to the supply of an information signal. In addition, the position of the defect, e.g. related to the longitudinal direction of the timber, is stored. The fault-free length can easily be determined from the distance covered between two detected faults or defects.

It is also particularly advantageous to use a CCD measuring line for optical scanning purposes. The output signals thereof can easily be processed and stored in a computer, whilst using a commercially available interface. In addition, the basic brightness setting and autofocussing can be relatively simply realized. It is particular advantageous if it is only necessary to set the fault threshold, i.e. the brightness difference from which a brightness change is to be detected as a fault.

According to a further advantageous development, a commercial colour video camera is used. Such a camera supplies a scanning signal already in line form. This can be fed to the computer and processed in on-line form. It is also possible to test objects having glossy surfaces. For example, it is possible to test or inspect for product and packaging errors see-through packs.

The level setting to the brightness of fault-free objects can e.g. take place in that initially a fault-free object is passed through the testing apparatus in a setting mode, when the average brightness value is determined and used as a reference for the further measurements.

If desired, the position of the defect, related to the axis of the CCD line or the like, can also be stored.

It is also possible to assess the objects from four sides, in that four inventive testing apparatuses are positioned to the left, right, above and below the object to be tested, such as e.g. sawn timber. Due to the fact that the object can engage on two of the four lateral faces, it is merely necessary to use two autofocussing devices on the two other testing apparatuses.

A further important advantage of the invention is that objects such as timber or rolled steel can be tested or inspected in virtually random length and thickness, that further there are no restrictions regarding the type of timber used and that it is also possible to store colour defects which could hitherto only be detected visually.

It is also very advantageous that the measured data can be stored in an integrated system, in which it is also possible to carry out the measures necessary for business purposes, apart from storing the defect, the quality, the dimensions and the storage location of each piece of timber.

The inventive testing apparatus can be advantageously used on automated production installations. For example, it is possible to monitor the operating area of robots, to establish whether there is anything of a moving nature therein. It is also possible to effect a safety disconnection, if the detected object is a person.

It is possible to monitor objects produced in a production line to establish the precise position of shape features, such as bores and recesses. It is also possible to monitor transparent materials, such as television tubes, drinking glasses or the like during production. It is also possible to test or inspect objects having a polished or even glossy surface, such as hammer finish.

With particular advantage light is applied obliquely to the surface to be detected, which makes it possible to determine surface unevenesses due to the shadow formation.

Colour defects on glazed tiles and the like can be detected by colour value determination using video cameras and compared with a given actual colour pattern, it being possible to remove faulty tiles immediately after the detection time, or to arrange them in different quality categories on the basis of the detected information signals.

Appropriately there is a group-forming detection of the information signals by the computer, it being possible to detect lack of uniformity of the structure, without extremely fast computers being necessary.

As a result of the real time processing possibility, it is possible, as desired, to process the detected signals in real time directly, i.e. without intermediate storage, or to intermediately store said signals and then in a following stage to read them out preferably at the same speed and convert them in the necessary way. It is possible to use for this purpose the known pipe lining and specific computers can be used for the necessary purposes. For example, it is possible within a computer-controlled production plant, to carry out the detection by front end processors, whilst also effecting data reduction and supplying the detected information signals from several front end processors to a central computer, which effects production control in an appropriate way.

Further details, features and advantages of the invention can be gathered from the following description of embodiments relative to the drawings, wherein show:

FIG. 1 A perspective view of a first embodiment of a testing apparatus, whereby in exemplified manner it is described in connection with sawn timber.

FIG. 2 A block circuit diagram of an embodiment of a measuring circuit for a testing apparatus according to FIG. 1.

FIG. 3 A block circuit diagram of another embodiment of the measuring circuit.

FIG. 4 A diagrammatic representation of part of the testing apparatus according to FIG. 1.

Figure 5:
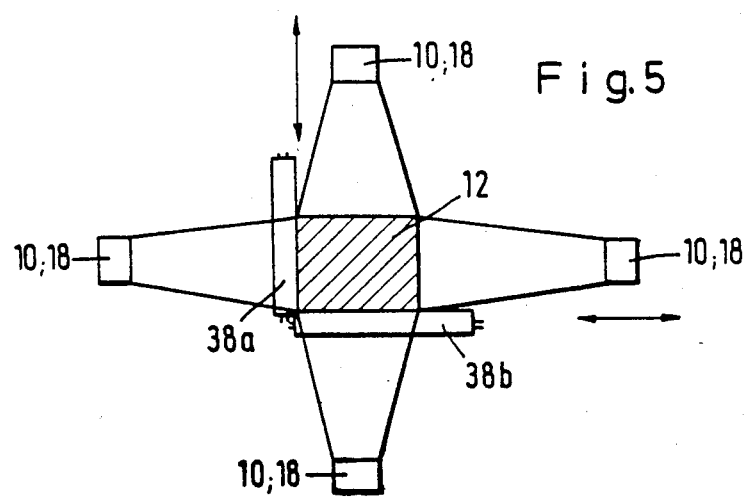

FIG. 5 A view of another embodiment of said testing apparatus.

Figure 6A:
Figure 6B:
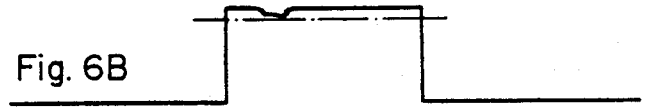
Figure 6C:
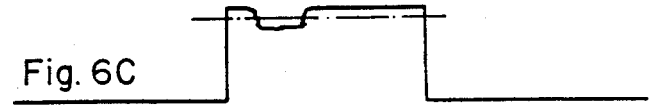

FIG. 6 Timing diagrams of the representation of measured signals, which occur in the measuring circuit according to FIG. 3.

In the embodiment shown in FIG. 1, there is a light source 10, which throws a light beam downward on to an object to be tested or inspected, such as a piece of sawn timber 12. Although the representation according to FIG. 1 shows vertical illumination, it is also possible to use oblique illumination or lighting, so as to permit better detection of surface unevenesses, such as holes. The piece of sawn timber 12 is longitudinally movable and is moved on not shown guidance means in the direction of arrow 14 at a speed of 3 m/s. The light beam from light source 10 is focussed on to the top surface of the timber 12, the light beam being conically widened at right angles to the main movement direction, i.e. to the longitudinal direction of timber 12, being more strongly focussed in the longitudinal direction of said timber. This makes it possible to obtain a relatively high light intensity.

Light source 10 is at such a distance from the surface 16 of timber 12 and therefore possibly the defect 15, that uniform illumination is obtained. An optical detection device 18 is positioned directly adjacent to light source 10. Optical detection device 18 has a lens 20, which is also focussed on to surface 16. The reciprocal arrangement of light source 10 and lens 20 is such that no measuring errors and in particular no parallax errors can occur. Thus, even when the timber is moved at a relatively high speed, a resolution of approximately 1 mm can be obtained.

During the movement of the timber, surface 16 is scanned linewise by the optical detection device 18, 0.3 m/s being available for each line. For converting the optical signals into electrical signals, high-speed semiconductor line cameras can be used. When there are reduced speed and/or resolution requirements, it is also possible to use less expensive optoelectrical converters.

It is possible to provide an optical and/or electric filter for the optical detection device 18, which makes it possible to block out disturbing influences and falsifications of the measured result.

As is further shown in FIG. 1, a support arm 100 is provided in the advance region of the sawn timber 12 to be detected and this forms part of the testing apparatus and receives the detection device 18 and light source 10. Support frame 100 can have a U-shaped profile with lateral longitudinal spars, which simultaneously form the feet for the support frame, together with an upper transverse spar, which carries the detection device 18 with light source 10, if the surface 16 of sawn timber 12 is to be detected. If the lateral face 16a, 16b are to be detected, then detection devices and light sources are provided on the vertical longitudinal spars of the support frame. If it is also necessary to detect the lower face 16c of the sawn timber 12, then use is made of an annular support frame 100, as shown in FIG. 1, which then also carries a detection device and a light source on its lower transverse spar. The supply of the object to be tested to the testing apparatus can take place by the direct introduction of the object to be tested or by means of a feed belt 150, which can be constructed as a conveyor belt driven in revolving manner.

If more than one face of the sawn timber 12 is to be detected, there is no need to illuminate each timber face by means of a separate light source. Instead, a corresponding number of reflecting mirrors 110 can be located in the optical path of the light source on support frame 100, so that one or more faces of the sawn timber can be illuminated. In the embodiment according to FIG. 1 by means of the reflecting mirrors fitted to support frame 100, surface 16 of the sawn timber is illuminated. If several faces of the sawn timber are illuminated by means of a light source 10, then with each illuminated face is associated a detection device 18. However, it is also possible to detect several sawn timber faces by means of a reflecting mirror system with only one detection device 18. By means of different light intensities, length of the light beam or illumination beam, it is possible to fix and individually determine the individual sawn timber faces and to store the detected values in such a way that they can subsequently be associated with the individual timber faces; the possibility also existing of detecting the individual different timber faces in rapid time sequence in rapid row sequences.

Light sources 10 can be in the form of all suitable light sources, particularly equidirectional light, monochromatic light, laser light, etc.

Support frame 100 receiving detection device 18 and light source 10 also carries further parts of the testing apparatus. The measuring circuit is then arranged in a casing 115, which can be connected to support frame 100.

In the embodiment of a measuring circuit shown in FIG. 2, a CCD scanner 22 is provided as the converter. CCD scanner 22 is connected via a suitable interface 24 to a microcomputer 26, which has a central processing unit CPU, a random access memory and a read only memory. Interface 24 serves as a matching circuit between CCD scanner 22 and microcomputer 26. Microcomputer 26 also has a control unit 28, which makes it possible to indicate the measured defects and the feeding in of parameters for controlling fault or defect detection. There is also a printer 30, which is able to supply a report on the tested or inspected timbers and which can simultaneously serve to detect entry into the store.

Preference is given to the use of a CCD scanner 22 with 500 to 2000 picture elements. By means of such a scanner, it is possible to scan larger timber surfaces. Scanning takes place in known manner, so that the input signal for interface 24 is present in serial form, an A/D conversion taking place in interface 24. The measured signal associated with each scanning period is supplied in digitized form to microcomputer 26, which checks whether a measured value exceeds the fault value threshold within the measured CCD line. It is particularly advantageous if a fault value indication occurring only with a single picture element is blocked out, because this would most probably be a reflection of a wood fibre.

Furthermore, an 8 bit resolution is adequate for the A/D converter, so that inexpensive technology can be used. The microcomputer can also be constructed as a single chip component with integrated control of the peripherals, which permits further cost saving. To ensure trouble-free operation, even under rough environmental conditions, the electronics can be designed in current-saving CMOS technology.

The semiconductor memory RAM used in microcomputer 26 can be constructed both for the intermediate storage of the detected defect points, whilst taking account of their size and position, and as a purely CPU-related main memory. The inventive measuring circuit can also be used as a front-end processor in a network and in particularly advantageous manner with a star or radial structure. However, in stand-alone operation, it is also possible to use an additional backing memory.

FIG. 3 shows another embodiment of the inventive measuring circuit, where the CCD scanner is replaced by a pickup tube VDK as the optical detection device 18. The output signal of the optical detection device 18 is fed to a voltage divider $P_1$, whose output is connected to the non-inverting input terminal of a comparator 30. The inverting input terminal of comparator 30 is connected to the output of a potentiometer $P_2$. The latter is used for the basic setting of the brightness value of the timber type used or for adapting to the light source used. Potentiometer $P_2$ is also connected in series with a control element 32, which can e.g. be constructed as a field effect transistor. Control element 32 permits an automatic adaptation to the timber type used. In addition, potentiometer $P_2$ is connected to ground across a resistor $R_1$.

The input terminal of control element 32 and the output terminal of comparator 30 are connected to microcomputer 26 across an integrated D/A-A/D converter 34.

Voltage divider $P_1$ is used for setting the sensitivity of the inventive measuring circuit for faults or defects, i.e. for setting the fault threshold. A further voltage divider is formed by a potentiometer $P_3$ and a resistor $R_2$ between operating voltage $+U_B$ and ground. The "cold" end of voltage divider $P_1$ is connected to the centre of the voltage divider formed by $P_3$ and $R_2$, so that the fault threshold can be fixed as a function of the setting of the voltage divider $P_1$ in relative manner, i.e. independently of the absolute value of the set brightness.

The embodiment of the measuring circuit shown in FIG. 3 permits the fully automatic testing of sawn timber, following the initial apparatus-specific adjustment of the trimming potentiometers $P_3$ and $P_4$. Control element 32 is set to a value corresponding to the basic brightness of the timber used. Firstly a faultless or almost faultless piece of timber of the type to be tested is measured in the setting mode of microcomputer 26 and its average brightness value is calculated by microcomputer 26 and used for the basic setting. This is followed by switching into the measuring mode and the desired fault or defect threshold is set by means of $P_1$. The defect threshold is generally dependent on the desired quality tolerance and therefore inter alia on the timber type used. It is then possible to test or inspect the entire batch or load at high speed and store the defect points.

FIG. 4 shows a particularly advantageous construction of optical detection device 18 in conjunction with light source 10. Use is made of a semitransparent mirror 36, which is obliquely positioned in the light beam from light source 10 to surface 16. After traversing the semitransparent mirror, the light beam from light source 10 strikes surface 16, where it is reflected. It then strikes the underside of the semitransparent mirror 36 and is reflected there, being passed to the optical detection device 18. This construction permits a particular accurate measurement of the position of defects.

FIG. 5 shows another embodiment of the testing apparatus. The piece of sawn timber 12 to be tested is a squared timber, whose edges all have to be inspected. For this purpose use is made of four light sources with four optical detection devices, each of which is arranged over one of the cut edges. Only two of the detection devices are provided with autofocussing mechanisms, because due to the guide rolls used the distance from the timber surface of the two other detection devices is always the same.

In FIG. 6 is shown at (a) the output signal of an optical detection device in the case of a single-line scanning of a faultless piece of timber. At (b) a defect point is reached, which can be noticed by a lower amplitude in part of the measured signal. However, the amplitude has still not dropped below the fault threshold. At (c) is shown the measured signal during the scanning of a measured line, which fully detects the fault point. An information signal is supplied and the fault position stored. The length-related storage takes place in that microcomputer 26 measures the time between the leading edge of the piece of timber which has just passed through up to the appearance of the information signal. Due to the constant advance rate, this time is length-proportional and consequently corresponds to the length of the fault free piece of timber.

In another not shown embodiment, it is possible to test or inspect objects provided with a glossy surface covered with hammer finish. For this purpose, use is made of a colour camera, which supplies information signals detected in line form. A video-speed special processor carries out a preprocessing and feature extraction. Hammer finish is particularly difficult to test, because it is firstly a glossy surface and secondly it is in more or less regular form. In the case of such objects the testing function is often to detect colour errors, as well as corrosion-aiding cracks in the finish structure. Shadows are cast by oblique lighting and they permit a distinction between a crack and the points in the hammer finish interpreted as dark by the camera. Thus, a threshold-oriented processing is possible for establishing cracks in the finish surface and for detecting colour errors.

In another embodiment of the inventive testing apparatus, it is possible to check for different faults dragee strips or cork plates. In the case of dragee strips, which comprise an aluminum strip, with tablets regularly distributed along the same, each being covered by a welded over see-through foil, e.g. packaging errors can occur, or individual tablets may be missing. It is necessary to detect minor grey value differences due to the reflection of the see-through foil. Thus, high resolution cameras or other optical detection means are required for providing the information signal.

In the case of cork plates, a uniform distribution of the light and dark points is required. The arrangement in different quality classes, as a result of the rapid processing, makes it necessary to use high-speed special processors. It is particularly advantageous to install several processors operating in parallel, because all the processing and transfer processes can be performed in synchronized manner.

In the last-mentioned use examples, the video camera is appropriately connected across a specially constructed interface 24. The latter has the A/D converter and using a per se known solution with an EPROM, it is possible to correct the characteristic, so as to linearize it with respect to the zero point and steepness. In place of the EPROM, in the case of different configurations used, it is possible to use for shading correction purposes a random access memory which can be loaded by the computer. If desired, laser scanners can be connected to said interface, in place of the video camera.

I claim:

1. Testing apparatus for detecting differently formed surfaces of objects, such as ceramic articles, articles made from glass, wood, plastics, objects packed in see-through foil, comprising:
   an illuminating device
   a conveyor for moving the object to be tested and the illuminating device relative to each other in a main movement direction, said illuminating device serving for simultaneously illuminating the object along an illuminated plane at right angles to the main movement direction with substantially uniform intensity,
   an optical detection device located adjacent said plane for simultaneously detecting a reflected optical characteristic of the object along the entire illuminated plane, and
   means for responding to changes of the reflected optical characteristic in the illuminated plane of the object detected by said detection device during the relative movement of object and said optical detection device.

2. Testing apparatus according to claim 1, characterized in that the optical detection device is connected to a computer for interpreting the information signal, which detects and indicates features occurring in the surface of the tested objects.

3. Testing apparatus according to claim 2, characterized in that computer has a memory for sequentially storing as information signals the features which occur.

4. Testing apparatus according to claim 3, characterized in that the computer has a time measuring device for measuring the time from the detection of the leading edge, considered in the main movement direction, of an object relative to the testing arrangement until a feature occurs and that the time measuring device is connected to a memory.

5. Testing apparatus according to claim 2, characterized in that a matching circuit for setting at least one recognition threshold for the information signal.

6. Testing apparatus according to claim 5, characterized in that the matching circuit, has an electronic control element for matching the optical detection device to different basic brightnesses of the surface of the object or the light source for utilizing the maximum dynamics of the optical detection device.

7. Testing apparatus according to claim 2, characterized in that the optical detection device includes a filter for increasing the sensitivity to particular optical characteristics.

8. Testing apparatus according to claim 1, characterized in that said illuminating device includes a light source for illuminating the object in the plane at right angles to the main movement direction in a conical path along a narrow zone, which extends over the entire length of the object in the plane, the light source emitting light having a predetermined characteristic.

9. Testing apparatus according to claim 1, characterized in a support frame (100) for supporting one of said optical detection device and said illuminating device.

10. Testing apparatus according to claim 1, characterized in that a support frame carries said illuminating device and said optical detection device said illuminating device including a light source and plurality of reflecting mirrors arranged in such a way that light source illuminates the object with substantially identical intensity, the optical detection device (18) being arranged for detecting the illuminating plane of the object via the reflecting mirror system.

11. Testing apparatus according to claim 1, characterized in that the object has substantially parallel lateral faces.

12. Method for testing objects with differently formed surfaces, such as ceramic products, objects made from glass, wood, plastic, articles packed in see-through foil, characterized in
   continuously moving the objects and an optical testing device in a main movement direction relative to each other,
   simultaneously illuminating a narrow zone extending over the width of the object in a plane at right angles to the main movement direction; detecting with the optical device an optical characteristic simultaneously along substantially the entire narrow zone, and responding to changes in the optical characteristic to the object at the plane to supply an information signal during the relative movement of object and optical detection device.

13. Method according to claim 12, characterized in that the information signal is stored in position-related manner with respect to each tested object.

14. Method according to claim 12 characterized in illuminating the surface of the object to be tested is so that the light beam from the light source forms an angle with respect to the light reflected by the surface to be tested and detected by the optical detection device which differs from zero and that the angle covered by the light beams is between 30° and 90°.

15. A test apparatus for objects, comprising:
   a radiant energy source
   a transport arrangement for moving the objects and the source relative to each other along a movement direction;
   said source being arranged for directing a fan shaped beam across an object transverse to the movement direction so that radiant energy is reflected by the object;
   an energy detector for detecting a characteristic of the energy reflected by the object simultaneously along the entire fan shaped beam across the object and for sensing changes in the detected characteristic in the energy reflected by the object along the entire fan shaped beam during relative movement of the object and the source.

16. A test apparatus as in claim 15, wherein said sensing means includes a computer for determining the location of the changes relative to the shape of the object on the basis of the relative speed of the source and object.

17. A test apparatus as in claim 16, wherein said sensing means includes means for setting a plurality of thresholds and comparing them to the changes in the detected characteristics.

* * * * *